United States Patent [19]

Boyce

[11] 4,309,303

[45] Jan. 5, 1982

[54] ALKYL NITRITE COMPOSITIONS

[76] Inventor: Walter F. Boyce, 58 Bayberry La., Westport, Conn. 06880

[21] Appl. No.: 119,169

[22] Filed: Feb. 6, 1980

[51] Int. Cl.$^3$ ................ C01B 21/50; C07C 77/00; C09K 15/06

[52] U.S. Cl. ................ 252/186; 149/118; 149/119; 260/466

[58] Field of Search ................ 252/186; 149/118, 119; 260/466

[56] References Cited

U.S. PATENT DOCUMENTS

| | | | |
|---|---|---|---|
| 2,927,939 | 3/1960 | Yunker et al. | 260/466 |
| 3,736,195 | 5/1973 | Burdette | 149/36 |
| 3,940,384 | 2/1976 | Teng et al. | 536/91 |
| 3,989,560 | 11/1976 | Allan | 149/36 |
| 4,002,515 | 1/1977 | Galvin | 149/36 |
| 4,035,569 | 7/1977 | Schweiger | 260/466 |
| 4,096,325 | 6/1978 | Teng et al. | 536/91 |

OTHER PUBLICATIONS

Chemical Abstracts, vol. 52 (1958), 5703b (French Patent No. 1,026,856 to Samuel).

*Primary Examiner*—Ben R. Padgett
*Assistant Examiner*—Irwin Gluck
*Attorney, Agent, or Firm*—Rasma B. Balodis

[57] ABSTRACT

This invention relates to a method of stabilizing liquid alkyl nitrites by adding ethyl hydroxyethyl cellulose, calcium silicate and mixtures thereof and mixing to produce solid state compositions and to stabilized compositions thereof.

5 Claims, No Drawings

ALKYL NITRITE COMPOSITIONS

BACKGROUND OF THE INVENTION

This invention relates to a method of stabilizing liquid alkyl nitrites by conversion to a solid state and to stabilized compositions thereof.

Liquid alkyl nitrite compounds, particularly isobutyl and isoamyl nitrites are powerful oxidizers and consequently, dangerous to handle. Shock may explode them. Heat may lead to violent decomposition reactions and fire. During storage in closed systems, degradation occurs with evolution of gas which may lead to detonation.

In the past, alkyl nitrites in the liquid state have been stabilized against degradation with small amounts of alkaline earth metal oxides, alkali metal carbonates and phosphates as described in U.S. Pat. No. 2,927,939 to Yunker et al.

It has been now discovered that liquid alkyl nitrites can be stabilized by converting to a solid state with the aid of ethyl hydroxyethylcellulose, calcium silicate and mixtures thereof. These solid state compositions have relatively low volatility and are less susceptible to degradation in comparison with liquid compositions. Consequently, the solid state compositions are safer to handle and to store reducing the risk of explosion.

The stabilized compositions retain their oxidizing properties and can be directly incorporated into propellant systems, household products and the like.

SUMMARY OF THE INVENTION

An object of the invention is to provide a method of stabilizing liquid alkyl nitrites selected from the group consisting of isobutyl nitrite and isoamyl nitrite by adding ethyl hydroxyethyl cellulose, calcium silicate and mixtures thereof to produce a solid state composition Another object of the invention is to provide stabilized, solid state alkyl nitrite compositions comprising about 70 to 80 percent by weight of alkyl nitrite selected from the group consisting of isobutyl nitrite and isoamyl nitrite and about 20 to 30 percent by weight of ethyl hydroxyethyl cellulose, calcium silicates and mixtures thereof.

DETAILED DESCRIPTION OF THE INVENTION

In accordance with the invention, liquid alkyl nitrites are converted to a solid state with the aid of certain inert materials which are compatible with the nitrite and produce no chemical reaction leading to decomposition and instability of the compositions. These conditions are satisfied by ethyl hydroxyethyl cellulose and calcium silicate both of which are chemically inert towards the alkyl nitrites.

Any ethyl hydroxyethyl cellulose may be used in preparing the solid state compositions of the invention. The preferred ethyl hydroxyethyl cellulose (EHEC) is one having a viscosity of 125 to 250 centipoises at 25° C. The term viscosity means viscosity of 5 percent solution of EHEC in a solvent mixture of 80 parts of toluene and 20 parts ethanol.

The calcium silicates of the invention can be selected from synthetic calcium silicates and diatomaceous earth. Particularly preferred is hydrous calcium silicate. The solid state compositions can be prepared either in gel form or in powder form depending on the applications desired.

The gel type structure is obtained by adding ethyl hydroxyethyl cellulose. The amount added will depend somewhat on the viscosity desired. Preferably, ethyl hydroxyethyl cellulose is added in the amount of about 20 to 30 percent by weight to maintain the gel structure of the composition during its shelf-life without developing syneresis. The formed gel has long shelf-life and displays stability towards temperature fluctuations and vibrational influences.

The powder form is prepared by adding to the liquid nitrite calcium silicate in the amount of about 20 to 30 percent by weight. The powders which are formed are flowable and easy to handle. For greater economy, part of the calcium requirement can be substituted by ethyl hydroxyethyl cellulose. The preferred mixtures comprise ethyl hydroxyethyl cellulose and calcium silicate in the ratio of about 1:1 to 2:3.

The following examples are intended to illustrate, but in no manner to limit the invention.

All percentages and parts in the disclosure and claims are based on weight unless otherwise indicated.

EXAMPLE I

Ninety ml. of isobutyl nitrite was placed in a Hobart mixer, 25g. of ethyl hydroxyethyl cellulose was added and the mixture blended at low speed. The composition produced was a firm, solid gel.

The composition was stored at room temperature for two months and examined visually. The composition retained its gel structure and no syneresis developed. There was no evidence of reaction such as bubble formation or discoloration.

EXAMPLE II

Twenty five g. of hydrous calcium silicate (Microcel E manufactured by Johns-Manville) was added to 90 ml. of isoamyl nitrite in a Hobart mixer. The mixture was blended at low speed to produce a powder with flowable characteristics. After two months of storage, there was no change in the characteristics of the powder.

EXAMPLE III

To 90 ml. of isobutyl nitrite was added 20g. of hydrous calcium silicate (Microcel E) and 5g. of ethyl hydroxyethyl cellulose. The mixture was blended in a Hobart mixer at low speed to produce a flowable powder. The powder retained its characteristics upon storage for two months.

What is claimed is:

1. A method of stabilizing liquid alkyl nitrites selected from the group consisting of isobutyl nitrite and isoamyl nitrite which comprises adding to the nitrites about 20 to 30 percent by weight of ethyl hydroxyethyl cellulose, calcium silicate or mixtures thereof and mixing to produce a solid state composition.

2. A method according to claim 1 whereas the mixture of ethyl hydroxyethyl cellulose and calcium silicate is in the ratio of about 1:1 to 2:3.

3. A solid state composition comprising about 70 to 80 percent by weight of alkyl nitrites selected from the group consisting of isobutyl nitrite and isoamyl nitrite and about 20 to 30 percent by weight of ethyl hydroxyethyl cellulose, calcium silicate or mixtures thereof.

4. A composition according to claim 3 wherein the mixture of ethyl hydroxyethyl cellulose and calcium silicate is in the ratio of about 1:1 to 2:3.

5. A composition according to claim 3 wherein the ethyl hydroxyethyl cellulose is in the amount of about 25 percent by weight.

* * * * *